(12) United States Patent
Sakakine et al.

(10) Patent No.: US 7,780,688 B2
(45) Date of Patent: Aug. 24, 2010

(54) SPRING CLIP AND METHOD FOR ASSEMBLING SAME

(75) Inventors: Ghassan Sakakine, Rancho Santa Margarita, CA (US); Donald L. Gadberry, San Clemente, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 469 days.

(21) Appl. No.: 10/543,800

(22) PCT Filed: Feb. 17, 2004

(86) PCT No.: PCT/US2004/004816

§ 371 (c)(1),
(2), (4) Date: Jul. 29, 2005

(87) PCT Pub. No.: WO2004/080275

PCT Pub. Date: Sep. 23, 2004

(65) Prior Publication Data

US 2006/0195125 A1    Aug. 31, 2006

Related U.S. Application Data

(60) Provisional application No. 60/452,574, filed on Mar. 6, 2003.

(51) Int. Cl.
*A61B 17/08* (2006.01)
(52) U.S. Cl. .................................. 606/157
(58) Field of Classification Search .......... 606/120, 606/151, 152, 153, 157, 158
See application file for complete search history.

(56) References Cited

U.S. PATENT DOCUMENTS 2,720,688 A * 10/1955 Torrani ..................... 24/567

(Continued)

FOREIGN PATENT DOCUMENTS

DE    67 50 390    1/1969

(Continued)

OTHER PUBLICATIONS

European Patent Office, Supplementary European Search Report for European Patent Application No. 0471940 9 dated Nov. 7, 2007.

(Continued)

*Primary Examiner*—Long V Le
*Assistant Examiner*—Saurel J Selkin
(74) *Attorney, Agent, or Firm*—John F. Heal; David G. Majdali (57) ABSTRACT

A surgical clip assembly is provided having two molded components and a tension spring. In one aspect, the spring clip includes a first molded portion having a first jaw and a first finger tab, a second molded portion coupled to the first molded portion and having a second jaw and a second finger tab, and a tension spring coupled to both the first and second molded portions. The first and second molded portions may be identical components. The tension spring is wound at least one turn forming a central coil and two extensions, and each of the molded portions is formed with a hinge area. Each of the hinge areas includes a hinge stud and a hinge cavity. The hinge areas align and snap-fit with one another to form the clip assembly. The extensions of the tension spring may be mounted into guide slots or ribs of the molded portions.

27 Claims, 5 Drawing Sheets

U.S. PATENT DOCUMENTS

| | | | | |
|---|---|---|---|---|
| 3,192,585 | A * | 7/1965 | Montag | 24/343 |
| 3,579,751 | A * | 5/1971 | Jonckheere | 606/158 |
| 3,802,437 | A | 4/1974 | Kees | |
| 3,996,937 | A * | 12/1976 | Williams | 606/158 |
| 4,614,008 | A * | 9/1986 | Brill et al. | 24/501 |
| 4,722,120 | A | 2/1988 | Lu | |
| 5,304,183 | A * | 4/1994 | Gourlay et al. | 606/142 |
| 5,415,666 | A * | 5/1995 | Gourlay et al. | 606/142 |
| 5,423,831 | A * | 6/1995 | Nates | 606/120 |
| 6,299,621 | B1 * | 10/2001 | Fogarty et al. | 606/151 |
| 2002/0111643 | A1 * | 8/2002 | Herrmann et al. | 606/158 |

FOREIGN PATENT DOCUMENTS

| | | |
|---|---|---|
| EP | 0 256 966 | 2/1988 |
| EP | 256966 A2 * | 2/1988 |
| WO | WO 98/00068 | 1/1998 |

OTHER PUBLICATIONS

Co-Pending U.S. Appl. No. 11/954,457, filed Dec. 12, 2007; Title: Surgical Clip.

Co-Pending U.S. Appl. No. 10/935,967, filed Sep. 8, 2004; Title: Surgical Clip.

Co-Pending U.S. Appl. No. 10/612,631, filed Jul. 2, 2003; Title: Interlocking Suture Clinch.

Co-Pending U.S. Appl. No. 10/533,398, filed Apr. 30, 2005; Title: Surgical Staple-Clip and Applier.

Co-Pending U.S. Appl. No. 11/280,098, filed Nov. 15, 2005; Title: Partial Occlusion Surgical Guide Clip.

Co-Pending U.S. Appl. No. 10/702,871, filed Nov. 5, 2003; Title: Suture Securing Device and Method.

Co-Pending U.S. Appl. No. 10/986,993, filed Nov. 12, 2004; Title: Overmolded Grasper Jaw.

Co-Pending U.S. Appl. No. 10/817,259, filed Apr. 2, 2004; Title: Suture Clip With Stop Ribs and Method for Making Same.

* cited by examiner

SPRING CLIP AND METHOD FOR ASSEMBLING SAME

This is a non-provisional application claiming the priority of provisional application Ser. No. 60/452,574 filed Mar. 6, 2003, entitled "Spring Clip and Method for Assembling Same", which is fully incorporated herein by references.

BACKGROUND OF THE INVENTION

1. Field of the Invention

This invention generally relates to surgical clips and clamps and, more specifically, to an improved surgical spring clip and an improved method for assembling such a clip.

2. Discussion of the Prior Art

Clips and clamps are commonly used in surgical procedures to interrupt or inhibit fluid flow in various body tissues and/or conduits such as arteries, veins and ducts. These clips have been formed with generally rigid parallel jaws, each of which is attached to a respective barrel portion. The barrel portions have been telescopically movable relative to each other to house a compression spring. Finger tabs have been attached to the barrel portions generally at their outermost extremities to open and close the jaws. The clips of the past have had a very high profile which has been dictated by the length of the barrel portions. As a result, this configuration of the surgical clips of the prior art has made them particularly unsuited for use in peripheral vascular surgery or in the working channels of access devices such as trocars and endoscopes. Even when elongate surgical clip appliers have been used, the relatively high profile of the barrel portions and tabs has been even further increased. Since the arms of the appliers must necessarily engage the barrel portions and tabs on outer surfaces, the use of appliers only increases the height of the applier/clip combination. Other clips have also been used but have been costly to assemble. As such, there is a need in the art for a low-profile surgical clip that is easy to assemble and is constructed from very few components. It is desirable that the clip may be used in peripheral vascular procedures and with minimally invasive access devices.

SUMMARY OF THE INVENTION

In accordance with the present invention, the deficiencies of the prior art have been overcome with an easy-to-assemble clip including only two molded components and a tension spring. In one aspect of the present invention, the spring clip includes a first molded portion having a first jaw and a first finger tab, a second molded portion coupled to the first molded portion and having a second jaw and a second finger tab, and a tension spring coupled to both the first and second molded portions to hold the clip assembly together. The first and second molded portions may be identical components. The first and second molded portions are moveable by operation of the first and second finger tabs between a generally closed position and a generally open position. In particular, moving the finger tabs together opposes the bias on the tension spring and moves the jaws to the open state. When the finger tabs are released, they expand to their maximum height as the tension spring moves the jaws to their closed state.

The tension spring comprises one or more turns and the finger tabs may include cavities or grooves to facilitate engagement with the fingers of a user or the jaws of a clip applier. That is, the spring clip may be manually actuated or remotely actuated using a clip applier. It is appreciated that the spring clip may be of any size and shape in accordance with the needs and requirements of each surgical procedure. It is further appreciated that the tension spring may be made of different wire materials, wire diameters, wire cross-section shapes and coil turns to provide the various tensions, strengths and other holding characteristics of the clip. The wire material may be of a specific hardness or temper to provide specific strength and tension properties. In another aspect of the invention, the jaws of the clip may be shaped, curved, bent or otherwise configured to provide access to specific areas of a procedure. Each of the jaws may be provided with a pad or an integral jaw pattern that operates to reduce trauma and/or increase traction with a target body conduit or tissue.

In accordance with a preferred process of the invention, the tension spring is wound at least one turn forming a central coil and two extensions, and each of the first and second molded portions is formed with a hinge area. Each of the hinge areas of the first and second molded portions includes a hinge stud and a hinge cavity. The hinge areas operate to align with each other and may include a snap-fit feature that couples with the other hinge area. After the first and second molded portions are aligned and fitted with each other, a housing portion is formed between the hinge areas to hold the central coil of the tension spring. With the assembly process of the invention, the extensions of the tension spring may be mounted into guide slots or ribs of either the jaws or the finger tabs of the first and second molded portions as the tension spring is placed into the housing portion. With this assembly process, different tension springs having various strength and tension properties may be used in accordance with the needs and requirements of each surgical procedure without changing the construction of the molded portions. The spring clip may be adapted for insertion through a tube having a working channel such as an endoscope, a trocar or any other access device extending across a body wall.

These and other features and advantages of the invention will become more apparent with a discussion of preferred embodiments in reference to the associated drawings.

DESCRIPTION OF PREFERRED EMBODIMENTS AND BEST MODE OF THE INVENTION

Figure 1:
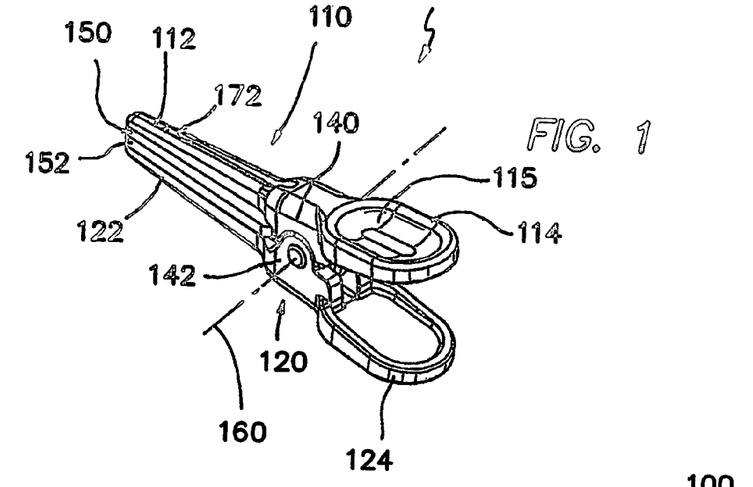
FIG. 1 is a perspective view illustrating a jaw spring clip in accordance with a first embodiment of the present invention.
Figures 2, 3:
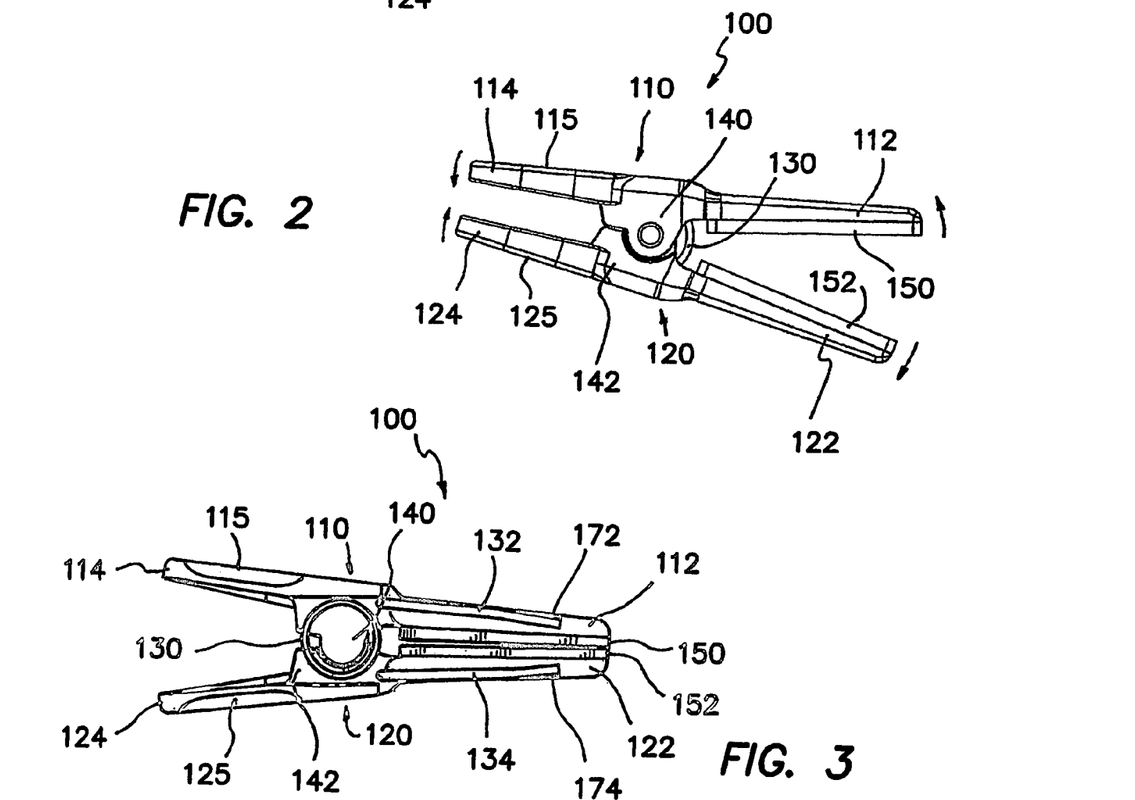
FIG. 2 is a side view of the jaw spring clip of FIG. 1 in an open position.
FIG. 3 is a section view of the jaw spring clip of FIG. 1 in a closed position.
Figure 4:
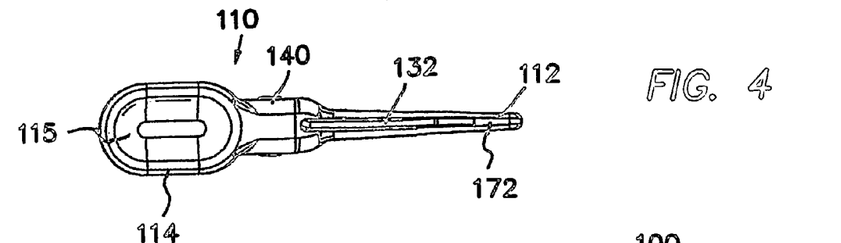
FIG. 4 is a top view of the jaw spring clip of FIG. 1.

FIGS. 1-6 illustrate a jaw spring clip 100 in accordance with the first embodiment of the present invention. The spring clip 100 includes a first molded portion 110 having a first jaw 112 and a first finger tab 114, a second molded portion 120 coupled to the first molded portion 110 and having a second jaw 122 and a second finger tab 124, and a tension spring 130 coupled to both the first and second molded portions 110, 120 to hold the clip assembly together. The first and second molded portions 110, 120 may be molded into any low profile and/or narrow width configuration to suit a user's need. In addition, the first and second molded portions 110, 120 may be identical components. The first and second jaws 112, 122 are relatively movable between a first relatively proximate position as illustrated in FIG. 3 and a second relatively spaced position as illustrated in FIG. 2. The first and second molded portions 110, 120 are moveable by operation of the first and second finger tabs 114, 124 between a first position wherein the jaws 112, 122 are generally closed (FIG. 3) and a second position wherein the jaws 112, 122 are generally open (FIG. 2). In particular, moving the finger tabs 114, 124 together opposes the bias on the tension spring 130 and moves the jaws 112, 122 to the open state. When the finger tabs 114, 124 are released, they expand to their maximum height as the tension spring 130 moves the jaws 112, 122 to their closed state.

The tension spring 130 has an axial axis 160 and comprises one or more turns. The finger tabs 114, 124 may include cavities or grooves 115, 125, respectively, to facilitate engagement with the fingers of a user or the jaws of a clip applier. That is, the spring clip 100 may be manually actuated or remotely actuated using a clip applier—applying the jaws of the clip applier between the finger tabs 114, 124, and operating the clip applier to open and close those finger tabs 114, 124. It is appreciated that the spring clip 100 of the present invention may be of any size and shape in accordance with the needs and requirements of each surgical procedure, e.g., peripheral vascular surgery, laparoscopic surgery, etc. It is further appreciated that the tension spring 130 may be made of different wire materials, wire diameters, wire cross-section shapes and coil turns to provide the various tensions, strengths and other holding characteristics of the clip 100. The wire material may be of a specific hardness or temper to provide specific strength and tension properties.

In another aspect of the invention, the jaws 112, 122 may be shaped, curved, bent or otherwise configured to provide access to specific areas of a procedure. That is, the jaws may be shaped to a variety of shapes in accordance with the intended use of the clip. Each of the jaws 112, 122 can be provided with a coating, such as a pad, or an integral jaw pattern 150, 152, such as a serrated surface, respectively, that operates to reduce trauma and/or increase traction with a target body conduit or tissue. The inserts 150, 152 may be molded in place or attached using any known adhesive.

Figures 5, 6, 7:
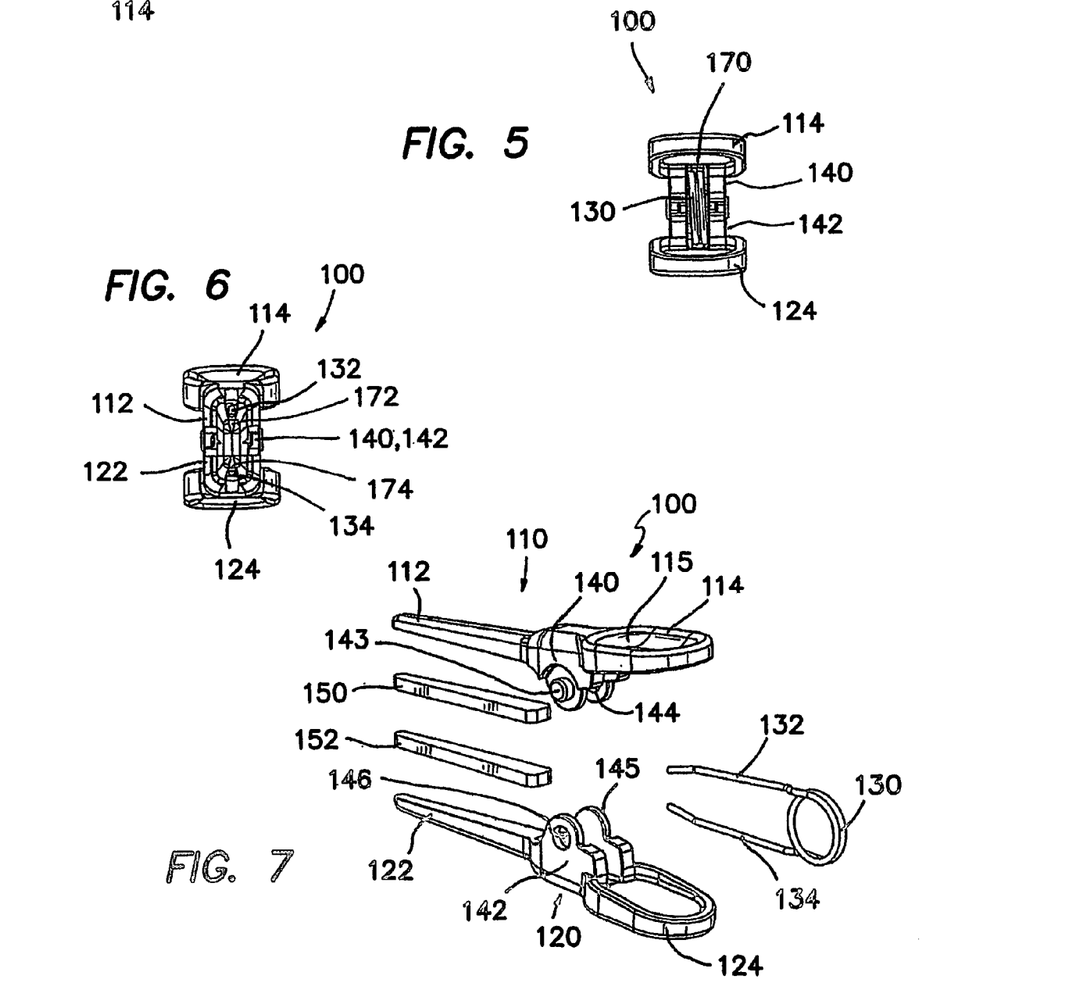
FIG. 5 is a proximal end view of the jaw spring clip of FIG. 1.
FIG. 6 is a distal end view of the jaw spring clip of FIG. 1.
FIG. 7 is an assembly view of the jaw spring clip of FIG. 1.

Referring to FIG. 7, various steps in the process of assembling the spring clip 100 are illustrated. In accordance with a preferred process of the invention, the tension spring 130 is wound at least one turn forming a central coil and two extensions 132, 134, and each of the first and second molded portions 110, 120 is formed with a hinge area 140, 142, respectively. The hinge area 140 of the first molded portion 110 includes a first hinge stud 143 and a first hinge cavity 144. Similarly, the hinge area 142 of the second molded portion 120 includes a second hinge stud 145 and a second hinge cavity 146. The hinge areas 140, 142 operate to align and may snap-fit with one another to form the spring clip 100. For example, the first and second molded portions 110, 120 are illustrated in a spaced relationship. In an initial step of the assembly process, the hinge areas 140, 142 of the first and second molded portions 110, 120, respectively, are aligned against each other such that the first hinge stud 143 fits into the second hinge cavity 146 and the second hinge stud 145 fits into the first hinge cavity 144. The hinge areas 140, 142 may include stops to limit the opening of the jaws 112, 122.

Figures 8, 9:
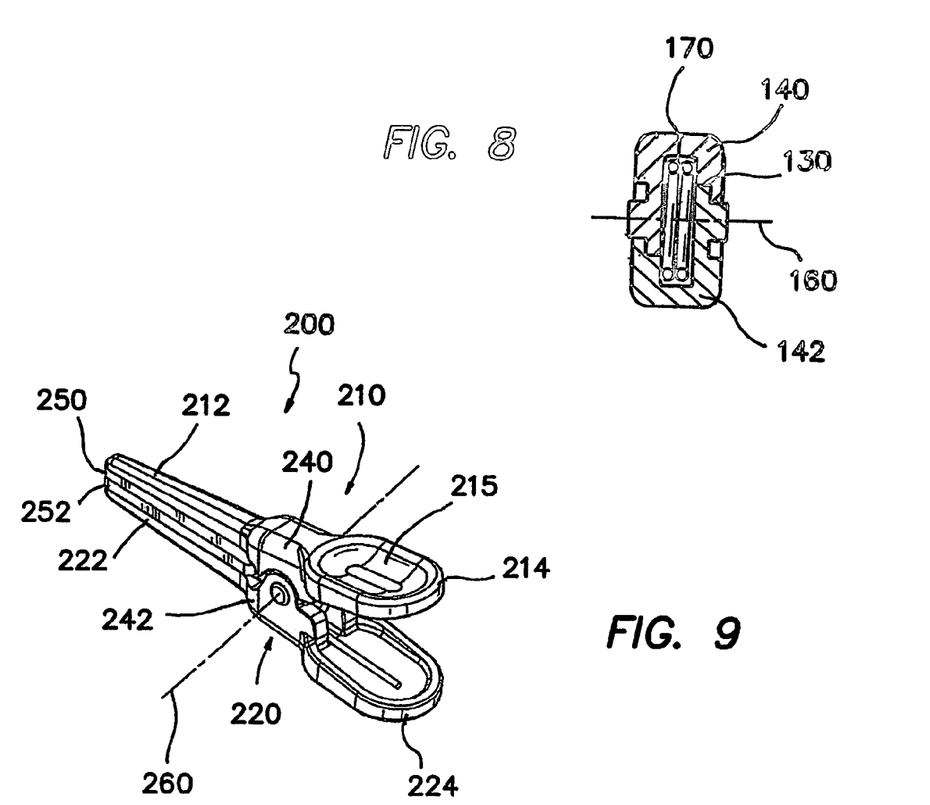
FIG. 8 illustrates the hinge features of the assembled clip.
FIG. 9 is a perspective view illustrating a finger tab spring clip in accordance with another embodiment of the present invention.

After the first and second molded portions 110, 120 are aligned and fitted with each other, a housing portion 170 is formed between the hinge areas 140, 142 as illustrated in FIGS. 5 and 8 to house the central coil of tension spring 130. Referring to FIG. 3, extensions 132, 134 of the tension spring 130 may be mounted into guide slots or ribs 172, 174 of jaws 112, 114, respectively, as the tension spring 130 is mounted into housing portion 170 to hold the spring clip assembly together. The spring extensions may provide bias loading to close the jaws or function as a cantilever strength member to the jaws, in addition to providing a backbone to the molded portions. With the assembly process of the invention, different tension springs having various strength and tension properties may be used in accordance with the needs and requirements of each surgical procedure without changing the construction of the molded portions. Thus, an advantage associated with the present clip is its low profile construction where a variety of tension springs may be mounted into the housing portion 170 between the hinge areas 140, 142 of the first and second molded portions 110, 120, respectively. It is appreciated that the spring clip 100 may be adapted for insertion through a tube having a working channel such as an endoscope, a trocar or any other access device extending across a body wall.

Figure 16:
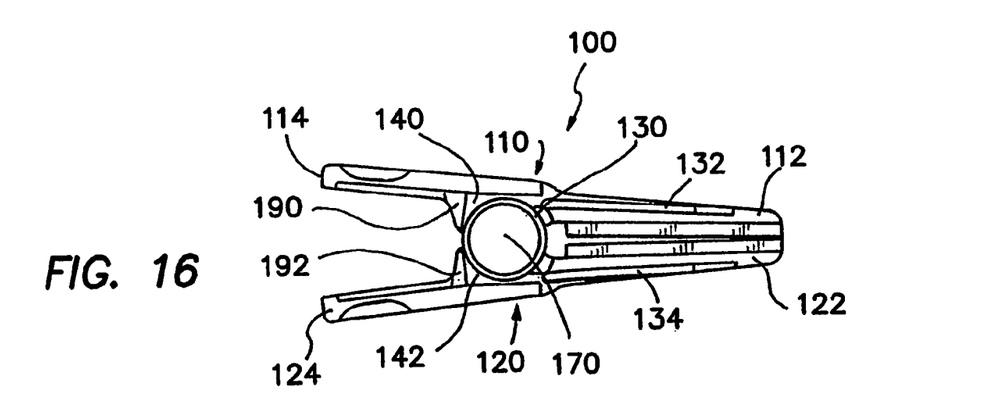
FIG. 16 is a side section view of a jaw spring clip including spring retainer ribs.
Figure 17:
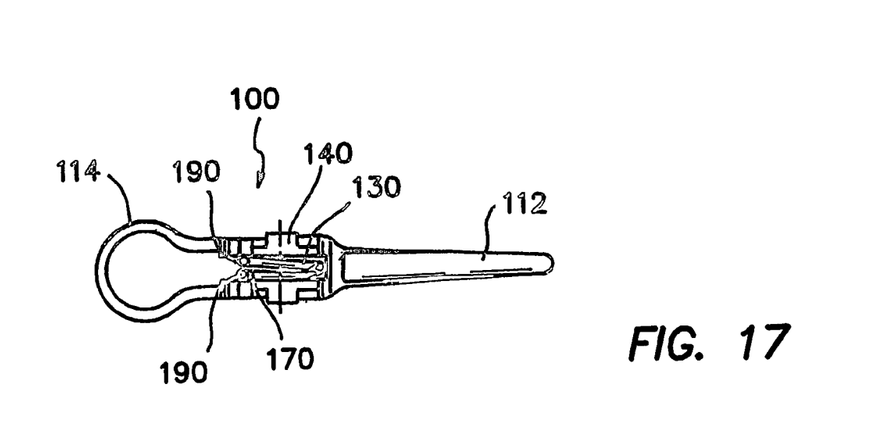
FIG. 17 is a top section view of a jaw spring clip including spring retainer ribs.

In yet another aspect of the invention, the hinge areas 140, 142 of the first and second molded portions 110, 120 may further include spring retainer ribs 190, 192, respectively, that operate to hold the central coil of tension spring 130 in place as illustrated in FIGS. 16 and 17. During assembly, the central coil may be compressed slightly to pass the ribs 190, 192, and once inside the housing portion 170, the central coil expands so as not to slip out of the retainer ribs. It is appreciated that each of the first and second molded portions 110, 120 may include a plurality of the retainer ribs.

Figure 10:
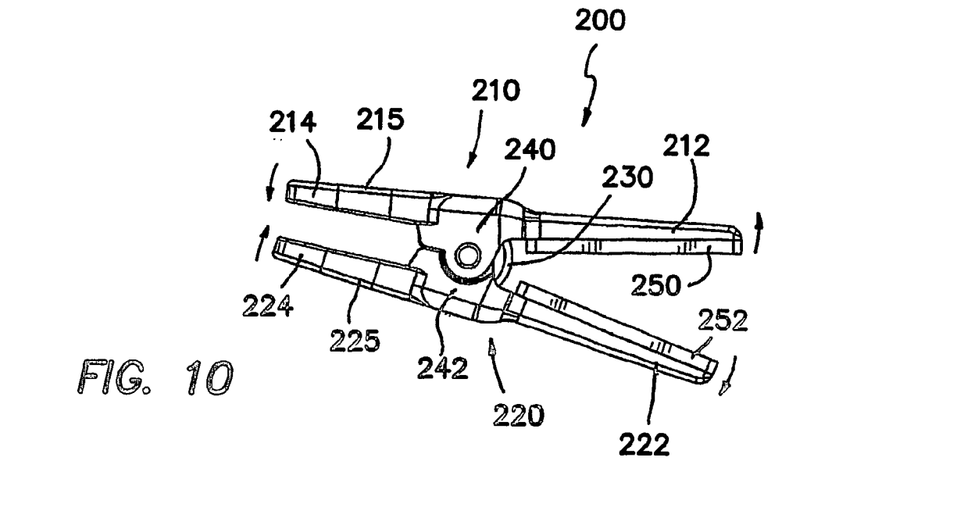
FIG. 10 is a side view of the finger tab spring clip of FIG. 9 in an open position.
Figure 11:
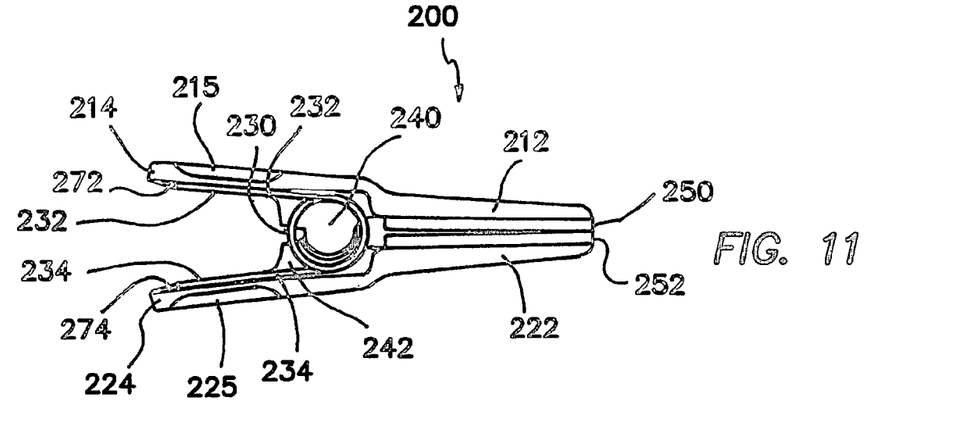
FIG. 11 is a section view of the finger tab spring clip of FIG. 9 in a closed position.
Figure 12:
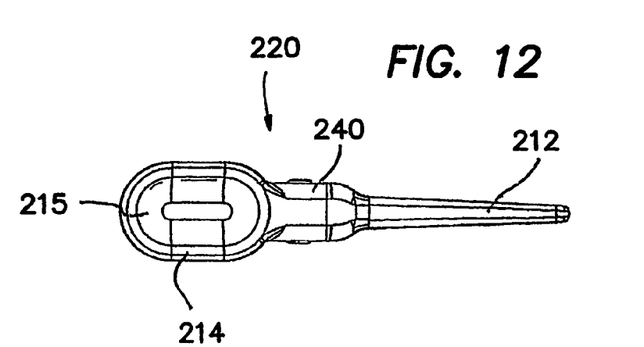
FIG. 12 is a top view of the finger tab spring clip of FIG. 9.

FIGS. 9-15 illustrate a finger tab spring clip 200 in accordance with another embodiment of the present invention. Similar to the spring clip 100 of the first embodiment, the spring clip 200 includes a first molded portion 210 having a first jaw 212 and a first finger tab 214, a second molded portion 220 coupled to the first molded portion 210 and having a second jaw 222 and a second finger tab 224, and a tension spring 230 coupled to both the first and second molded portions 210, 220 to hold the clip assembly together. The first and second molded portions 210, 220 may be molded into any low profile and/or narrow width configuration to suit a user's need. In addition, the first and second molded portions 210, 220 may be identical components. The first and second jaws 212, 222 are relatively movable between a first relatively proximate position as illustrated in FIG. 11 and a second relatively spaced position as illustrated in FIG. 10. The first and second molded portions 210, 220 are moveable by operation of the first and second finger tabs 214, 224 between a first position wherein the jaws 212, 222 are generally closed (FIG. 11) and a second position wherein the jaws 212, 222 are generally open (FIG. 10). In particular, moving the finger tabs 214, 224 together opposes the bias on the tension spring 230 and moves the jaws 212, 222 to the open state. When the finger tabs 214, 224 are released, they expand to their maximum height as the tension spring 230 moves the jaws 212, 222 to their closed state.

The tension spring 230 has an axial axis 260 and comprises one or more turns. The finger tabs 214, 224 may include cavities or grooves 215, 225, respectively, to facilitate engagement with the fingers of a user or the jaws of a clip applier. Like the clip 100 in the first embodiment, the clip 200 may be manually actuated or remotely actuated using a clip applier. It is appreciated that the spring clip 200 of the present invention may be of any size and shape in accordance with the needs and requirements of each surgical procedure, e.g., peripheral vascular surgery, laparoscopic surgery, etc. It is further appreciated that the tension spring 230 may be made of different wire materials, wire diameters, wire cross-section shapes and coil turns to provide the various tensions, strengths and other holding characteristics of the clip 200. The wire material may be of a specific hardness or temper to provide specific strength and tension properties.

In another aspect of the invention, the jaws 212, 222 may be shaped, curved, bent or otherwise configured to provide access to specific areas of a procedure. That is, the jaws may be shaped to a variety of shapes in accordance with the intended use of the clip. Each of the jaws 212, 222 can be provided with a coating, such as a pad, or an integral traction pattern 250, 252, respectively, that operates to reduce trauma and/or increase traction with a target body conduit or tissue. The inserts 250, 252 may be molded in place or attached using any known adhesive. The coating may include at least one of soft elastomer, Kraton, PVC, and polyisoprene.

Figure 15:
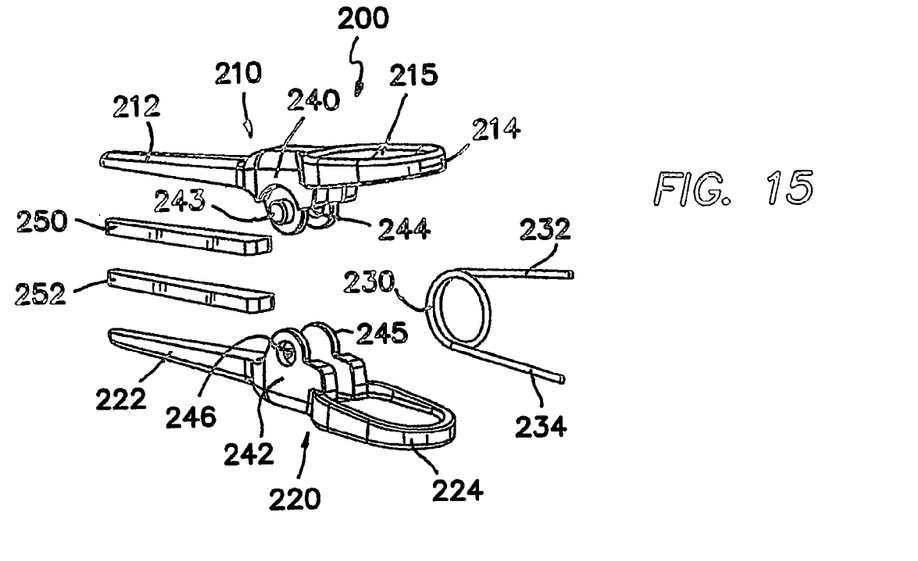
FIG. 15 is an assembly view of the finger tab spring clip of FIG. 9.

Referring to FIG. 15, various steps in the process of assembling the spring clip 200 are illustrated. In accordance with a preferred process of the invention, the tension spring 230 is wound at least one turn forming a central coil and two extensions 232, 234, and each of the first and second molded portions 210, 220 is formed with a hinge area 240, 242, respectively. The hinge area 240 of the first molded portion 210 includes a first hinge stud 243 and a first hinge cavity 244. Similarly, the hinge area 242 of the second molded portion 220 includes a second hinge stud 245 and a second hinge cavity 246. The hinge areas 240, 242 operate to align and may snap-fit with one another to form the spring clip 200. For example, the first and second molded portions 210, 220 are illustrated in a spaced relationship. In an initial step of the assembly process, the hinge areas 240, 242 of the first and second molded portions 210, 220, respectively, are aligned against each other such that the first hinge stud 243 fits into the second hinge cavity 246 and the second hinge stud 245 fits into the first hinge cavity 244. The hinge areas 240, 242 may include stops that limit the opening of the jaws 212, 222.

Figure 13:
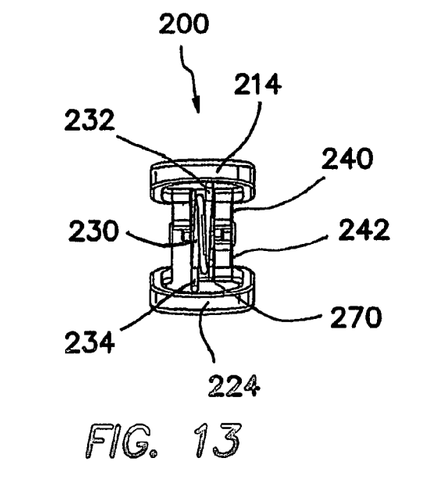
FIG. 13 is a proximal end view of the finger tab spring clip of FIG. 9.
Figure 14:
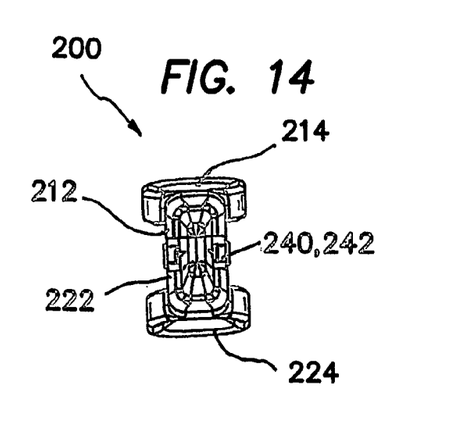
FIG. 14 is a distal end view of the finger tab spring clip of FIG. 9.

After the first and second molded portions 210, 220 are aligned and fitted with each other, a housing portion 270 is formed between the hinge areas 240, 242 as illustrated in FIG. 13 to house the central coil of tension spring 230. Referring to FIG. 11, extensions 232, 234 of the tension spring 230 may be mounted into guide slots or ribs 272, 274 of finger tabs 214, 224, respectively, as the tension spring 230 is mounted into housing portion 270 to hold the spring clip assembly together. The spring extensions may provide bias loading to close the jaws or function as a cantilever strength member to the jaws, in addition to providing a backbone to the molded portions. With the assembly process of the invention, different tension springs having various strength and tension properties may be used in accordance with the needs and requirements of each surgical procedure without changing the construction of the molded portions. It is appreciated that the spring clip 200 may be adapted for insertion through a tube having a working channel such as an endoscope, a trocar or any other access device extending across a body wall.

There are many variations in the foregoing concept which will be apparent to those skilled in the art. As discussed above, materials can vary significantly, although in the preferred embodiment, elements other than the tension spring are formed by injection-molded thermoplastic, and the tension spring is formed of stainless steel wire. The pads or inserts can also vary widely in different embodiments of the invention. In one example, the pads may have a foam rubber substrate that is covered with a mesh structure, which facilitates traction with a body conduit such as a vessel. Another example would be to mold a traction pattern directly into the jaws. It will be understood that many other modifications can be made to the various disclosed embodiments without departing from the spirit and scope of the invention. For these reasons, the above description should not be construed as limiting the invention, but should be interpreted as merely exemplary of preferred embodiments.

The invention claimed is:

1. A surgical clip comprising:
   a first molded portion having a first jaw, a first finger tab, and a first guide slot extending generally longitudinally with respect to the first molded portion and a first hinge area integrally formed therewith and extending transverse to the first jaw and the first finger tab, the first hinge area comprising at least one first spring retainer rib;
   a second molded portion coupled to the first molded portion such that a portion of the first molded portion and a portion of the second molded portion define a housing therebetween, and the second molded portion having a second jaw, a second finger tab, and a second guide slot extending generally longitudinally with respect to the second molded portion and a second hinge area integrally formed therewith and extending transverse to the second jaw and the second finger tab, the second hinge area comprising at least one second spring retainer rib; and
   a tension spring formed of a wire and comprising a central coil, a first spring extension extending from the central coil, and a second spring extension extending from the central coil opposite the first spring extension, the tension spring positioned such that at least a portion of the central coil is housed within the housing and held in place within the housing by the first and second spring retainer ribs acting on an outer surface of the central coil, at least a portion of the first spring extension extends through the first guide slot, and at least a portion of the second spring extension extends through the second guide slot;
   wherein the second molded portion is identical to the first molded portion.

2. The surgical clip of claim 1, wherein the first and second molded portions are moveable by operation of the first and second finger tabs between a generally closed position and a generally open position.

3. The surgical clip of claim 2, wherein the first and second jaws are resiliently pressed against each other in the closed position.

4. The surgical clip of claim 1, wherein the tension spring includes at least one turn.

5. The surgical clip of claim 1, wherein at least one of the first and second molded portions includes a plurality of cavities to facilitate engagement of fingers of a user.

6. The surgical clip of claim 1, wherein at least one of the first and second molded portions includes a plurality of grooves to facilitate engagement with jaws of a clip applier.

7. The surgical clip of claim 6, wherein the clip is remotely actuated using the clip applier.

8. The surgical clip of claim 1, wherein the clip is manually actuated.

9. The surgical clip of claim 1, wherein the tension, strength and holding characteristics of the tension spring may be varied based on at least one of the number of turns of a central coil, the hardness or temper of the wire, the material of the wire, the diameter of the wire and the cross-section of the wire.

10. The surgical clip of claim 1, wherein the wire has a cross-section having an oval, circular, square, rectangular or any geometric shape.

11. The surgical clip of claim 1, wherein each of the first and second jaws further comprises a pad or insert that operates to reduce trauma.

12. The surgical clip of claim 11, wherein the pads or inserts are molded in place or attached using any known adhesive.

13. The surgical clip of claim 11, wherein the pads or inserts include a rubber substrate covered with a mesh substrate.

14. The surgical clip of claim 1, wherein the first and second jaws are serrated to provide improved traction.

15. The surgical clip of claim 1, further comprising a coating over the first and second jaws to provide improved traction and padding.

16. The surgical clip of claim 1, wherein the first hinge area comprises a first hinge stud and a first hinge cavity, the second hinge area comprises a second hinge stud and a second hinge cavity, and the first and second hinge areas are couplable to define the housing therebetween.

17. A method of forming a surgical clip, comprising:
winding a single wire around a support member or mandrel at least one turn forming a central coil, a first extension and a second extension of a tension spring;
providing a first molded portion having a first jaw, a first finger tab and a first hinge area, and a second molded portion having a second jaw, a second finger tab and a second hinge area, wherein the first hinge area includes a first hinge stud, a first hinge cavity, and a first spring retainer rib and the second hinge area includes a second hinge stud, a second hinge cavity, and a second spring retainer rib, and the second molded portion being identical to the first molded portion;
aligning the first hinge area with the second hinge area and fitting the first hinge stud into the second hinge cavity and the second hinge stud into the first hinge cavity; and
positioning the tension spring between the first hinge area and the second hinge area such that the central coil is externally held by the first spring retainer rib and the second spring retainer rib.

18. The method of claim 17, wherein each of the first and second hinge areas includes a snap-fit feature that couples with one another.

19. The method of claim 17, wherein each of the first and second molded portions includes a housing portion to hold the central coil of the tension spring.

20. The method of claim 19, wherein each of the first and second molded portions comprises at least one of guide slots and ribs, and further comprising mounting the extensions of the tension spring into the guide slots or ribs of either the jaws or the finger tabs of the first and the second molded portions as the tension spring is placed into the housing portion of the first and second molded portions.

21. The method of claim 17, wherein positioning the tension spring further comprises:
compressing the spring;
advancing the central coil of the tension spring past the first spring retainer rib and the second spring retainer rib; and
allowing the central coil to expand between the first hinge area and the second hinge area.

22. The method of claim 17, further comprising coating the first and second jaws with at least one of an atraumatic and a traction-enhancing material.

23. The method of claim 22, wherein the coating comprising at least one of soft elastomer, Kraton, PVC, and polyisoprene.

24. The method of claim 17, further comprising placing disposable inserts over the first and second jaws to improve traction.

25. The method of claim 17, wherein different tension springs having various strength and tension properties may be used in accordance with the needs and requirements of each surgical procedure.

26. The method of claim 17, wherein each of the first and second hinge areas further includes spring retainer ribs for holding the central coil of the tension spring in place.

27. The method of claim 17, wherein the wire has a cross-section having an oval, circular, square, rectangular or any geometric shape.

* * * * *